United States Patent [19]

Kida et al.

[11] Patent Number: 5,359,372
[45] Date of Patent: Oct. 25, 1994

[54] CONTACT LENS FOR INTRAOCULAR OBSERVATION

[75] Inventors: Hideki Kida; Shinji Ishiguro; Toshiharu Morino, all of Nagoya, Japan

[73] Assignee: Tomey Corp., Nagoya, Japan

[21] Appl. No.: 21,463

[22] Filed: Feb. 23, 1993

[51] Int. Cl.$^5$ .............................................. A61B 3/00
[52] U.S. Cl. ...................................... 351/219; 351/205
[58] Field of Search ....................... 351/205, 211, 219; 359/440

[56] References Cited

U.S. PATENT DOCUMENTS

| | | | |
|---|---|---|---|
| 3,820,879 | 6/1974 | Frisen | 351/205 |
| 4,134,647 | 1/1979 | Ramos-Caldera | 351/205 |
| 4,367,018 | 1/1983 | Abe | 351/205 |
| 4,439,026 | 3/1984 | Wilms | 351/219 |
| 4,750,829 | 6/1988 | Wise | 351/219 |
| 5,046,836 | 9/1991 | Volk | 351/205 |
| 5,189,450 | 2/1993 | Crossman et al. | 351/219 |
| 5,252,998 | 10/1993 | Reis et al. | 351/205 |
| 5,255,025 | 10/1993 | Volk | 351/205 |

FOREIGN PATENT DOCUMENTS

| | | | |
|---|---|---|---|
| 49-13039 | 3/1974 | Japan . | |
| 5-22304 | 2/1993 | Japan | 351/219 |
| 1623647 | 1/1991 | U.S.S.R. | 351/219 |

*Primary Examiner*—Richard E. Gluck
*Assistant Examiner*—Howard R. Richman
*Attorney, Agent, or Firm*—Oblon, Spivak, McClelland, Maier & Neustadt

[57] ABSTRACT

A contact lens for intraocular observation capable of optically recognizing an inner portion of an eyeball by contacting the contact lens on a surface of a cornea of an eye to be inspected through a light ray transmitted through an inner portion of the contact lens comprising: an optical path dividing member provided on an optical path for leading a light ray incident on the inner portion of the contact lens to the eye to be inspected for dividing a portion of the light ray on said optical path; and an index provided at a position approximately optically conjugate with a portion to be observed of the eye to be inspected on a divided optical path divided by the optical path dividing member. The portion to be observed and said index can optically be recognized by at least partially superposing a first image of the index on a second image of the portion to be observed.

1 Claim, 5 Drawing Sheets

CONTACT LENS FOR INTRAOCULAR OBSERVATION

BACKGROUND OF THE INVENTION

1. Field of the Invention

This invention relates to a contact lens for intraocular observation which is employed in diagnosis or medical treatment of an eyeball and is capable of optically recognizing an inner portion of an eyeball such as an anterior chamber angle portion, an eyeground portion and the like.

In diagnosis or medical treatment of an eye in ophthalmology, there is a case wherein observation of an inner portion of an eyeball is necessitated. For instance, with respect to the anterior chamber angle portion situated on the periphery of an anterior chamber of the eyeball, an abnormality such as in width, in opening degree or in adhesion thereof, relates to a degree of intraocular pressure, generation of glaucoma or the like. With respect to the disc optic situated on the eyeground of the eyeball, an abnormality in a size thereof or the like relates to generation of the various illnesses or the like. Accordingly, the diagnosis of an eye is carried out by observing the anterior chamber angle portion or the disc optic.

Furthermore, it is difficult to directly perform the observation of the inner portion of the eyeball. Therefore, generally, a so-called contact lens for intraocular observation which can optically recognize the inner portion of the eyeball by contacting the contact lens on the surface of a cornea of an eye to be inspected through a light ray transmitted through the inner portion of the contact lens, has been in use. As for the contact lens for intraocular observation, various constructions thereof such as a beam-transmitting type, a beam-reflecting type or the like have conventionally been proposed, as shown in Japanese Examined Patent Publication No. 13039/1974, which is selectively employed in accordance with a portion to be observed.

Concerning the diagnosis of an eye or the like, there is a case wherein an angle of opening of the anterior chamber angle portion or dimensions of the disc optic or the like should specifically be measured, as stated above, as well as optically recognizing the inner portion of an eyeball.

In that case, to obtain high measurement accuracy, it is necessary to perform direct measurement of an image of the inner portion of an eyeball which is observed through the contact lens for intraocular observation, by optically recognizing the image by superposing a pertinent index such as a protractor, a scale or the like, on the image of the inner portion of an eyeball.

It can be suggested that for instance, a pertinent index is provided on an optical path between the contact lens and an observer (ophthalmologist or the like), at outside the contact lens for intraocular observation, such that the image of the inner portion of an eyeball which is observed through the contact lens, and such an index can be optically recognized by superposing them.

However, the observation employing the contact lens is normally carried out by employing a microscope or the like. Therefore, the index should be provided inside of the microscope or the like, which is difficult to install.

Moreover, even when the index can be provided inside of the microscope, since the index should be changed for measuring an angle, for measuring a distance or the like, in accordance with the portion to be observed in an eye, the changing operation is troublesome.

Furthermore, in employing the index for measuring a distance, since the portion to be observed is magnified by the microscope, the scale of the index should be converted at every time when the magnification of the microscope is changed. This operation is troublesome which hampers smooth observation or diagnosis.

SUMMARY OF THE INVENTION

This invention has been performed with the background of the above situation. It is an object of the present invention to provide a contact lens for intraocular observation capable of clearly optically recognizing a portion to be observed of an eye to be inspected and a pertinent index by simultaneously superposing them by an easy and simple operation.

According to an aspect of present invention, there is provided a contact lens for intraocular observation capable of optically recognizing an inner portion of an eyeball by having the contact lens contact a surface of a cornea of an eye to be inspected through a light ray transmitted through an inner portion of the contact lens comprising: an optical path dividing member provided on an optical path for leading a light ray incident on the inner portion of the contact lens to the eye to be inspected for dividing a portion of the light ray on said optical path; and an index provided at a position approximately optically conjugate with a portion to be observed of the eye to be inspected on a divided optical path divided by the optical path dividing member; whereby said portion to be observed and said index can optically be recognized by at least partially superposing a first image of the index on a second image of the portion to be observed.

The contact lens for intraocular observation, is generally formed in accordance with the portion to be observed. In the contact lens for intraocular observation of this invention, it is possible to provide the index, such that the position of the index is conjugate with the position to be observed of the eyeball which is optically recognizable by employing the contact lens of the present invention. Accordingly, both the portion to be observed and the index can optically be observed clearly in a state wherein the images of the portion to be observed and the index are mutually superposed.

In the invented contact lens for intraocular observation, since the index is provided at the inner portion of the contact lens, no special operation is required other than exchanging the contact lens in accordance with the portion to be observed.

Furthermore, in the invented contact lens for intraocular observation, since the index is provided at the inner portion of the contact lens, even when the magnification of the employed microscope is changed, the index can optically be recognized by the magnification the same with that of the portion to be observed. Accordingly, it is not necessary to perform the conversion or the like in accordance with the magnification.

DETAILED DESCRIPTION OF THE PREFERRED EMBODIMENTS

A detailed explanation will be given of embodiments of the present invention in reference to the drawings, to specifically clarify the present invention further, as follows.

Figure 1:
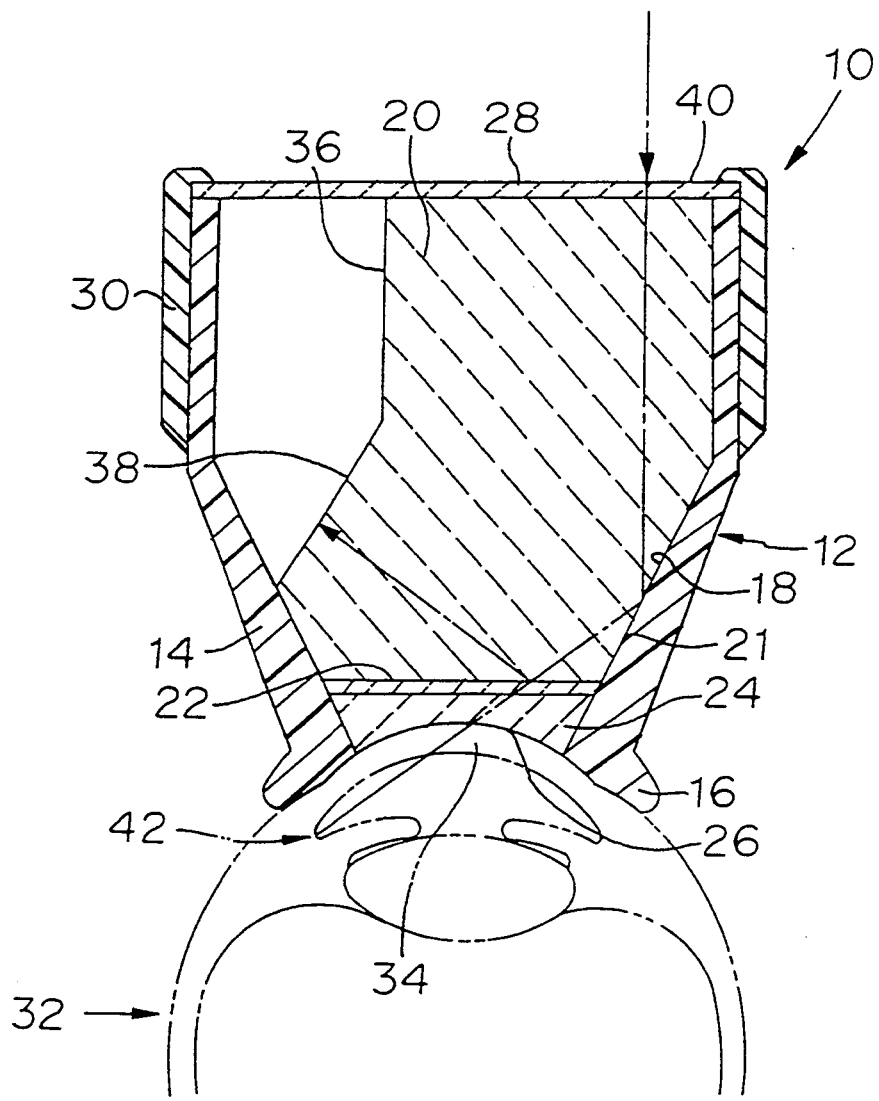
FIG. 1 is an explanatory diagram showing a section of an embodiment of a contact lens for observing the anterior chamber angle portion.
Figure 2:
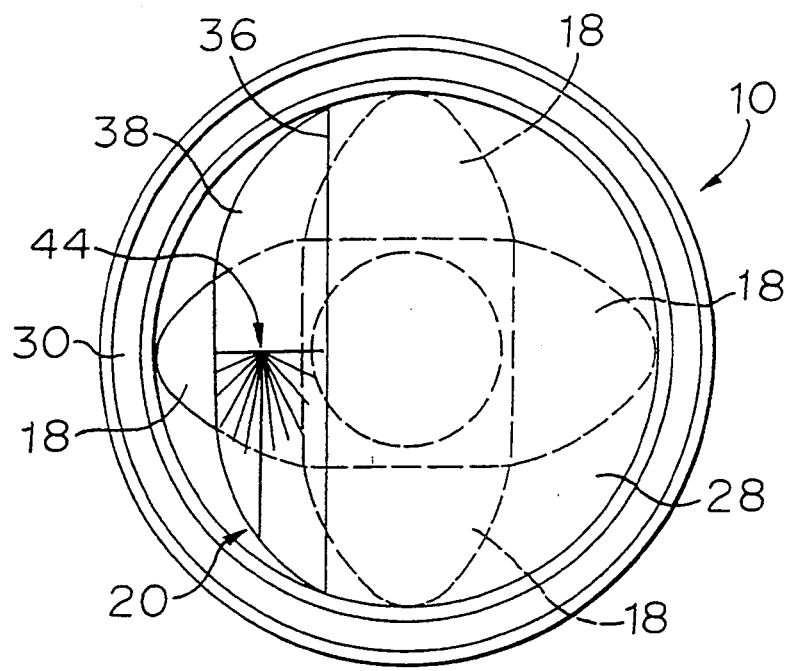
FIG. 2 is a plane view of the contact lens for observing the anterior chamber angle portion shown in FIG. 1.

First, FIG. 1 and FIG. 2 show a contact lens for observing the anterior chamber angle portion having a structure in accordance with the present invention. In FIG. 1 and FIG. 2, reference numeral 12 designates a housing, which is formed in an approximately hollow cylindrical form, as a whole. On one side in the axial direction of the housing 12 is a tapered cylinder 14 of which diameter is gradually reducing. A contact portion 16 in an approximately skirt-like form diverging outwardly, is provided integrally with a peripheral portion of an opening of the tapered cylinder 14.

Furthermore, the inner peripheral face of the tapered cylinder 14 in the housing 12, is composed of four flat inclined faces 18 which are disposed with a phase difference of 90° in the peripheral direction, and are slanted by a predetermined angle with respect to a plane orthogonal to an axis of the housing 12. The housing 12 is normally applied with optically intransparent coloring on the outer peripheral face, or is formed by an optically intransparent resin or the like, to prevent the incidence of outside light.

A lens 20 which is formed by a transparent material such as acrylic resin or the like, is accommodated in the inner portion of the housing 12. The lens 20 is formed in an outer configuration which approximately corresponds to the form of the inner peripheral face of the housing 12, wherein one side of an outer peripheral face of an edge portion thereof approximately inwardly taper in an axial direction. The outer peripheral face in the tapered form, is provided with four chamferings in correspondence with the inclined faces 18 of the housing 12. Furthermore, four sheets of reflecting mirror faces 21 are formed at the chamfered portions corresponding to the respective inclined faces 18, by coating aluminium by a method of vapor deposition or the like.

The lens 20 is inserted into the housing 12, and is integrally fitted and fixed thereto in a state wherein the lens 20 tightly contacts the respective inclined faces 18 provided in the housing 12.

In the lens 20, a half mirror 22 and a contact lens 24 are tightly laminated to each other on an edge face in the axial direction on the side wherein the lens 20 is downsized in the tapered form, which are integrated by accommodating them in the housing 12. The half mirror 22 is formed in a plane form by a transparent optical material. Furthermore, on the half mirror 22, a portion of an incident light is reflected and is divided into a transmitted light and a reflected light by forming an optical thin film treatment on a face on the side to be laminated with the lens 20. The contact lens 24 is formed by a transparent material similar to that of the lens 20 and constitutes a concave spherical form approximately corresponding to a shape of a surface of a cornea of an eyeball on the edge face of the contact lens 24 and the contact portion 16 of the housing 12. As shown in FIG. 1 by an imaginary line, an eye contact face 26 is formed which contacts the surface of a cornea 34 of an eye to be inspected 32, in observing the inner portion of the eyeball.

Furthermore, a plane transparent protective cover 28 is laminated on the other edge face in the axial direction on the side of the larger diameter in the lens 20 such that the protective cover 28 also covers an edge face of the housing 12 in the axial direction. By retaining the outer peripheral portion of the protective cover 28 by a cylinder-like fixing ring 30 which is fitted and fixed to the outer peripheral face of the housing 12, the protective cover 28 is integrated to the device. A face of the lens 20 on the side of the face laminated with the protective cover 28, is an incident face 40 wherein an illuminating light is incident thereon.

On the other hand, a cut-off portion 36 is provided in the lens 20 which is accommodated in the housing 12 as above, which is open at an edge face on the larger diameter side of the housing 12 thereof by a predetermined width. A bottom face of the cut-off portion 36 is an inclined face 38 opposing the half mirror 22 with an inclination of a predetermined angle and which is disposed opposing one of the reflecting mirror faces 21 provided on the outer periphery of the lens 20, in a direction orthogonal to an axis thereof.

Accordingly, as shown in FIG. 1, among the illuminating lights which are incident on the incident face 40 and are reflected by the reflecting mirror face 21, a light reflected by the half mirror 22 is projected to the inclined face 38. The angle of inclination of the inclined face 38 is set with respect to the half mirror 22 such that the illuminating light is incident on the inclined face 38 in an approximately vertical direction, by which the light reflected by the inclined face 38 is led to outside from the incident face 40, by passing through an optical path which is approximately the same with that of the incident light.

Furthermore, the inclined face 38 is disposed at a position which is approximately optically conjugate with the anterior chamber angle portion 42 of the eye to be inspected 32 as an object of the observation, which is illuminated with a light transmitted through the half mirror 22, under a state wherein the contact lens 10 contacts the cornea 34 of the eye to be inspected 32. In other words, a length of optical path between the half mirror 22 and the inclined face 38 is set to be approximately the same with a length of the optical path between the half mirror 22 and the anterior chamber angle portion 42 of the eye to be inspected 32. The length of optical path between the half mirror 22 and the anterior chamber angle portion 42 of the eye to be inspected 32, is normally determined by an average dimension of a general grown-up person.

Figure 3:
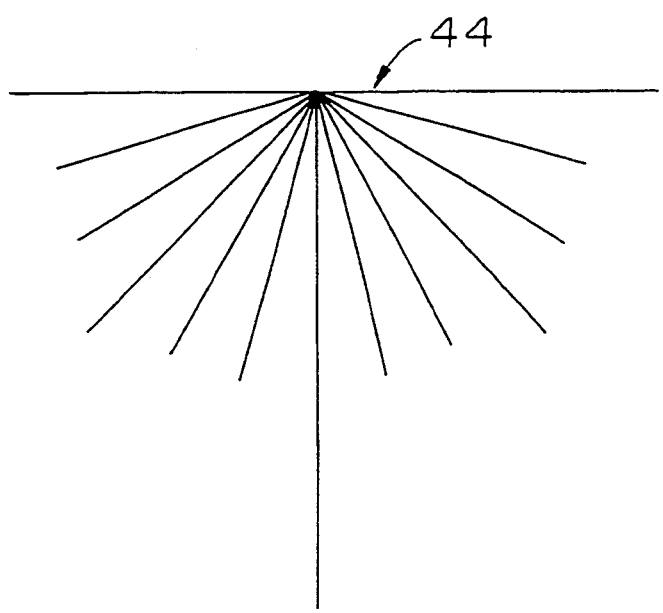
FIG. 3 is an explanatory front diagram showing an angle index which is provided in the contact lens for observing the anterior chamber angle portion shown in FIG. 1.

Furthermore, an angle index 44 is provided on the inclined face 38 which is set as above, and which functions as an angle measuring instrument. The angle index 44 can be formed by directly printing or marking the angle index 44 on the inclined face 38, or labeling a separate member on which the index is printed. Specifically in this example, as shown in an angle index 44 in a front view of FIG. 3, an angle index showing the angle by thirteen straight lines drawn at every angular interval of 15°.

Furthermore, it is preferable to employ color arrangement for the angle index 44, wherein the contrast is promoted which is represented by an example of black on white matrix or white on black matrix. Furthermore, the measuring operation is made possible and the optical recognition is clear and easy even when an amount of light reaching the index is small, by making the index by employing a material or a paint which is fluorescent or which can be provided with a sufficient brightness even when illuminated by a very small scattered light.

The surface of the cut-off portion 36 containing the inclined face 38 provided with the angle index 44, is colored, by which the incidence of an outside light from the surface of the cut-off portion 36 can be prevented.

Figure 4:
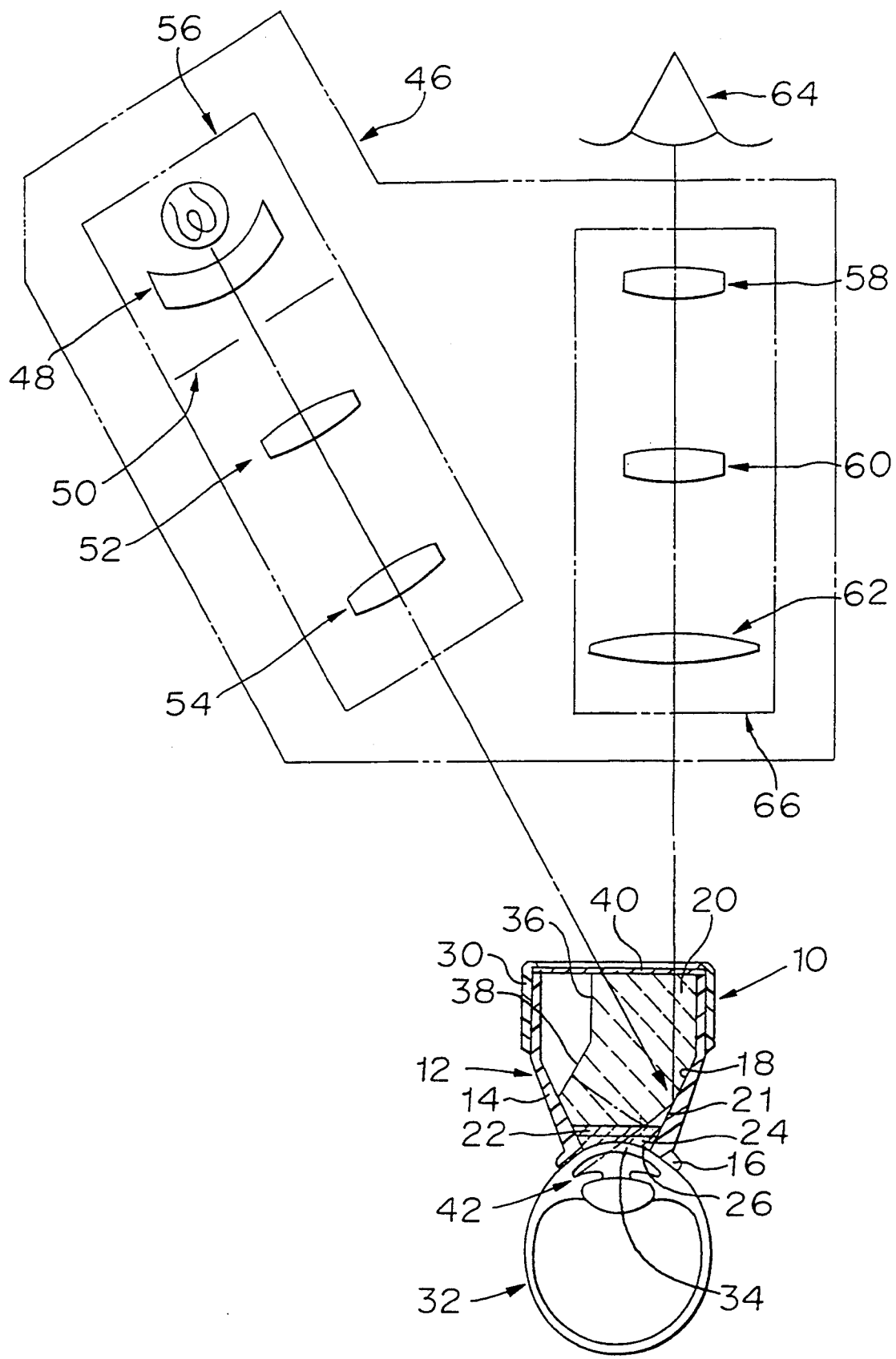
FIG. 4 is an explanatory diagram for explaining an example of a method of observing the anterior chamber angle portion employing the contact lens for observing the anterior chamber angle portion shown in FIG. 1.

In case of observing of the inner portion of an eyeball of a person to be inspected, by the contact lens 10 having the above construction, for instance, as approximately shown in FIG. 4, the observation is performed by retaining the eye contact face 26 of the contact lens 10 in a state wherein the eye contact face 26 contacts the surface of the cornea 34 of the eye to be inspected 32, and by employing a slit lamp microscope 46.

The slit lamp microscope 46 is provided with an illuminating optical system 56 wherein an illuminating light emitted from a light source 48 is converted into a slit-like light by a slit 50 and lenses 52 and 54, which is incident on the incident face 40 of the contact lens 10, and an observing optical system for leading a reflected light which is emitted from the incident face 40 of the contact lens 10, to an eye 64 of an inspecting person (observer), by magnifying the reflected light by lenses 58, 60 and 62, at a predetermined magnification.

The illuminating light which is projected from the illuminating optical system 56 of the slit lamp microscope 46, and which is incident on the lens 20 of the contact lens 10, after reflected by the reflecting mirror face 21, transmits through the half mirror 22 and the contact lens 24 and illuminates the anterior chamber angle portion 42 of the eye to be inspected 32, a portion of which is reflected on the surface of the half mirror 22, and illuminates the inclined face 38 provided with the angle index 44. As is clarified by the above, in this embodiment, an optical path dividing member is composed of the half mirror 22.

Furthermore, the lights reflected and scattered by the anterior chamber angle portion 42 and by the inclined face 38, are integrated on the same optical path again on the surface of the half mirror 22, reflected by the reflecting mirror face 18, and is led to the observing optical system 66 through the lens 20. In this way, the inspecting person can observe the anterior chamber angle portion 42 and the angle index 44 provided on the inclined face 38, in the same scope of vision, as mutually superposing images.

Accordingly, by employing the contact lens 10, the angle of the optically recognized anterior chamber angle portion 42, can directly be measured by the angle index 44, by which the high measurement accuracy can easily be obtained.

Since the angle index is provided inside the contact lens 10, it is not necessary to provide the index on the side of the slit light microscope 46 in case of the observation, by which the observation can be facilitated.

Since the angle index 44 is disposed at the position approximately optically conjugate with that of the anterior chamber angle portion 42 as an object of observation, both the image of the angle index 44 and the image of the anterior chamber angle portion 42 can optically be recognized clearly through the observing optical system 66, by which the excellent measurement accuracy can stably be obtained.

Figure 5:
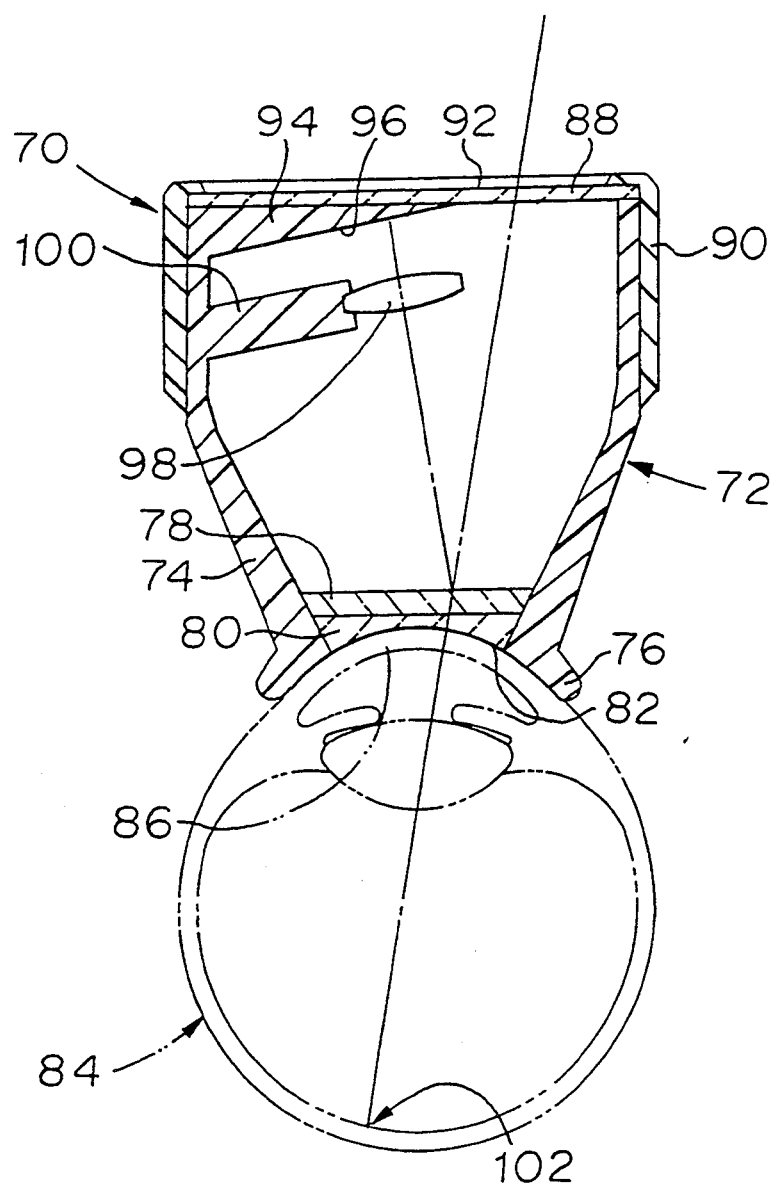
FIG. 5 is an explanatory sectional diagram showing another embodiment of a contact lens for observing the eyeground.

Next, FIG. 5 shows another embodiment of this invention of the contact lens for observing an eyeground having the construction according to the present invention.

In FIG. 5, a reference numeral 72 designates a housing which is formed in an approximately hollow cylindrical form as a whole. On one side of the housing 72 in the axial direction, is a tapered cylindrical portion 74 of which diameter is gradually reduced. A contact portion 76 having a skirt-like form diverging outwardly, is integrally provided at the peripheral portion of an opening of the tapered cylindrical portion 74.

Furthermore, the opening portion on the side of the tapered cylindrical portion 74 of the housing 72, is fixedly integrated with a half mirror 78 and a contact lens 80, in a state wherein the half mirror 78 and the contact lens 80 are laminated to each other, by accommodating them in the housing 72. The half mirror 78 is of a plate-like shape. By reflecting a portion of an incident light on one surface of the half mirror 78, the incident light is divided into a transmitted light and a reflected light. Furthermore, the contact lens 80 is formed by a light-transmittent material, which constitutes an eye contact face 82 having a concave spherical form approximately corresponding to a shape of a surface of a cornea of an eyeball by cooperating with the contact portion 76 of the housing 72. The eye contact face 82 contacts the surface of a cornea 86 of an eye to be inspected 84 in observing the inner portion of the eyeball.

A plate-like transparent protective cover 88 is provided at an opening of the housing 72 on the larger diameter side thereof in the axial direction. By retaining the outer peripheral portion thereof by a cylindrical fixing ring 90 which is fitted and fixed to an outer peripheral face of the housing 72, the protective cover 88 is integrally assembled into the device in a state wherein the protective cover 88 covers the opening portion of the housing 72. Furthermore, an incident face 92 on which an illuminating light is incident is constructed in the housing 72 on the protective cover 88.

On the other hand, a protruding wall 94 which protrudes from a surrounding wall of the housing 72 to the inner direction, is provided in the inner space of the housing 72 enclosed by the contact lens 80 and the protective cover 88 as above, which is disposed in the vicinity of an inner portion of the opening on the side of the larger diameter of the housing 72. The protruding wall 94 is disposed such that the protruding wall 94 partially covers the opening portion of the housing 72. An inner side face of the protruding wall 94 is an inclined face 96 opposing the half mirror 78 by an inclination of a predetermined angle.

In this way, as shown in FIG. 5, a light which is incident on the incident face 92, is reflected by the half mirror 78 and illuminates the inclined face 96. An angle of inclination of the inclined face 96 is set with respect to the half mirror 78 such that the illuminating light is incident on the inclined face 96 approximately vertically, by which the light reflected by the inclined face 96, is led to outside from the incident face 92, after passing through an optical path which is approximately the same with that of the incident light.

Furthermore, a convex lens 98 is disposed between the inclined face 96 and the half mirror 78 by being fixedly supported by a supporting portion 100 standing on the housing 72. Accordingly, an optical distance between the half mirror 78 and the inclined face 96 is set to be larger than an actual distance by the convex lens 98.

The inclined face 96 is disposed at a position which is approximately optically conjugate with the disc optic 102 of an eye to be inspected 84 as a portion of an object for the observation, which is illuminated with a light transmitted through the half mirror 78 under a state wherein the contact lens 70 contacts the cornea 86 of the eye to be inspected 84, by controlling the optical distance between the half mirror 78 and the inclined face 96 by the convex lens 98. In other words, a length of the optical path between the half mirror 78 and inclined face 96 is set to be approximately the same with a length of the optical path between the half mirror 78 and the disc optic 102 of the eye to be inspected 84.

Figure 6:
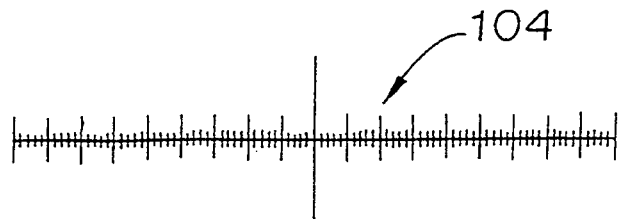
FIG. 6 is an explanatory front diagram showing a dimensional index which is provided on the contact lens for observing the eyeground shown in FIG. 5.

Furthermore, a dimensional index 104 shown in FIG. 6 is provided on the inclined face 96 which is set as above. The dimensional index 104 can be formed by directly printing or marking the dimensional index 104 on the inclined face 96, or by labeling a separate member on which the index is printed, or the like. Specifically, in this embodiment, as shown in a front diagram of FIG. 6, the dimensional index 104 designates the dimension by a great number of straight lines drawn at every constant interval.

Furthermore, in observing the disc optic at the inner portion of an eyeball of a person to be inspected, by the contact lens 70 having the above construction, for instance, the observation is performed by employing a slit lamp microscope approximately similar to that in the first embodiment, while maintaining a state wherein the eye contact face 82 of the contact lens 70 contacts the surface of the cornea 86 of the eye to be inspected 84.

In the observation, an illuminating light which is incident on the contact lens 70, transmits through the half mirror 78 and the contact lens 80, and illuminates the disc optic 102 of the eye to be inspected 84. A portion of the illuminating light is reflected by a surface of the half mirror 78, and illuminates the inclined face 96 on which the dimensional index 104 is provided. Moreover, as is clarified by the above description, in this embodiment, an optical path dividing member is constructed by the half mirror 78.

The lights which are reflected and scattered by the disc optic 102 and by the inclined face 96, are integrated on the same optical path on the surface of the half mirror 78, and the integrated light is led to the outside through the protected cover 88, by which an inspecting person can observe the disc optic 102 and the dimensional index 104 provided on the inclined face 96, in the same scope of vision, as mutually laminated images.

Accordingly, by employing the contact lens 70, the size of the optically recognizable disc optic 102 can directly be measured by the dimensional index 104, thereby easily providing the high measurement accuracy.

In the contact lens 70, the dimensional index 104 is disposed at a position which is approximately optically conjugate with that of the disc optic 102 as a portion for observation. Therefore, it is not necessary to prepare separately the index in the observation. Moreover, both the image of the dimensional index 104 and the image of the disc optic 102 can optically be recognized clearly through the observing optical system.

The dimensional index 104 can optically be recognized by magnifying the dimensional index 104 by the same magnification with that of the image of the portion to be observed (disc optic 102) by the observing optical system. Therefore, even in the case wherein the magnification of the observing optical system is changed, it is not necessary to convert a value provided based on the dimensional index 104, by which the smooth and easy observation can effectively be achieved.

In the contact lens 70 of the embodiment, the actual distance between the half mirror 78 and the inclined face 96 can be set smaller than the required optical length, by the convex lens 98 provided between the half mirror 78 and the inclined face 96. Therefore, this invention is provided with an advantage wherein a compact structure of the contact lens 70 can preferably be achieved.

The detailed explanation has been given to the embodiments of this invention as above. However, these embodiments are only literal examples. This invention should not be interpreted as limited by these specific examples.

Figure 7:
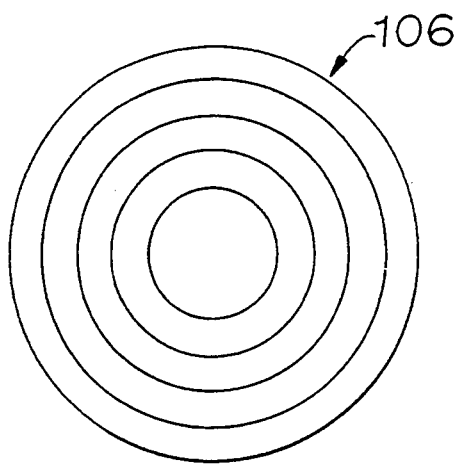
FIG. 7 is an explanatory diagram showing a specific example of an index which is preferably adopted in the contact lens for observing the inner portion of an eye according to the present invention.
Figure 8:
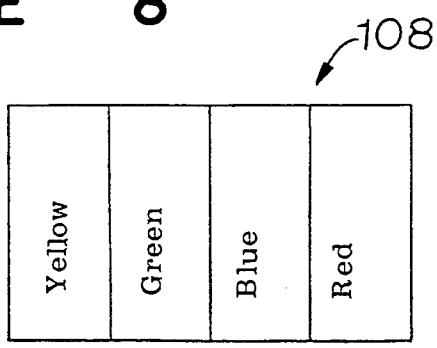
FIG. 8 is an explanatory diagram showing another specific example of an index which can preferably be adopted in the contact lens for observing the inner portion of an eye according to the present invention.
Figure 9:
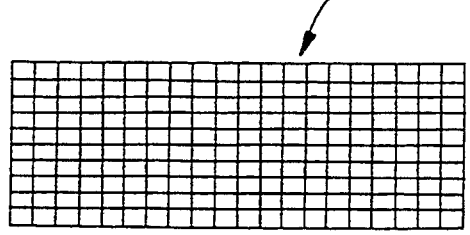
FIG. 9 is an explanatory diagram showing a specific example of an index which can preferably be adopted in the contact lens for observing the inner portion of an eye according to the present invention.

For instance, the shape of the index provided in the contact lens should pertinently be changed in accordance with the portion for observation or the like. Specifically, in measuring the size of the disc optic, other than the dimensional index in the second embodiment, it is possible to employ an index 106 having concentric circles at every predetermined interval as shown in the FIG. 7. Furthermore, as shown in FIG. 9, it is possible to employ an optical mark 110, having a lattice form provided with predetermined constant intervals. Or, when color at a predetermined portion in an eye is to be observed, it is possible to employ a pertinent color sample index 108, a shown in FIG. 8.

Furthermore, in the above embodiments, the specific examples are shown wherein this invention is applied to the contact lens for observing the anterior chamber angle portion and the disc optic. Other than these examples, it is naturally possible to apply this invention similarly to a contact lens for observing another portion in an eye.

Although not enumerating specifically, this invention can be performed in embodiments provided with various alternations, modifications, improvements or the like, based on the knowledge of the artisan to which this technology pertains. Furthermore, it goes without saying that these embodiments are included in the scope of this invention so far as the embodiments are not deviated from the gist of the present invention.

What is claimed is:

1. A contact lens for intraocular observation capable of optically recognizing an inner portion of an eyeball, wherein the contact lens contacts a surface of a cornea of an eye to be inspected and a light ray is transmitted through an inner portion of the contact lens, the contact lens comprising:

an optical path dividing member provided on an optical path for leading a light ray incident on the inner portion of the contact lens to the eye to be inspected for dividing a portion of the light ray on said optical path; and an index provided at a position approximately optically conjugate with a portion to be observed of the eye to be inspected on a divided optical path divided by the optical path dividing member;

whereby said portion to be observed and said index can optically be recognized by at least partially superposing a first image of the index on a second image of the portion to be observed.

* * * * *